United States Patent [19]

Markley et al.

[11] 4,349,568
[45] Sep. 14, 1982

[54] SULFUR-SUBSTITUTED DIPHENYL ETHERS HAVING ANTIVIRAL ACTIVITY

[75] Inventors: Lowell D. Markley, Midland, Mich.; Yulan C. Tong, Walnut Creek, Calif.; Steven G. Wood, Orem, Utah

[73] Assignee: The Dow Chemical Company, Midland, Mich.

[21] Appl. No.: 158,964

[22] Filed: Jun. 12, 1980

[51] Int. Cl.³ .................. A61K 31/135; A61K 31/10; C07C 43/263

[52] U.S. Cl. .......................... 424/330; 424/337; 564/430; 568/29; 568/31; 568/33; 568/36; 568/37; 568/43; 568/44; 568/47

[58] Field of Search .................. 568/29, 31, 33, 36, 568/37, 43, 44, 47; 564/430; 424/330, 337

[56] References Cited

U.S. PATENT DOCUMENTS

| | | | |
|---|---|---|---|
| 2,998,453 | 8/1961 | Nichols | 568/33 |
| 3,423,470 | 1/1960 | Herbele et al. | 260/612 |
| 3,766,238 | 10/1973 | Rohr | 260/465 F |
| 3,776,961 | 12/1973 | Theissen | 260/613 R |
| 3,813,444 | 5/1974 | Abe et al. | 568/36 |
| 3,821,312 | 6/1974 | Abe et al. | 568/36 |
| 3,957,865 | 5/1976 | Rohe et al. | 568/33 |
| 4,039,588 | 8/1977 | Wilson et al. | 260/613 R |
| 4,091,109 | 5/1978 | Aoki et al. | 568/36 |
| 4,156,011 | 5/1979 | Lafon et al. | 568/36 |
| 4,179,461 | 12/1979 | Marhold et al. | 568/33 |

OTHER PUBLICATIONS

Chem. Abstracts 67:116462q (1967).
Abstract of Swiss Pat. No. 8426 (7/07/77).

*Primary Examiner*—Mary C. Lee

[57] ABSTRACT

Novel compounds exhibiting antiviral activity are disclosed, such compounds are represented by the formula:

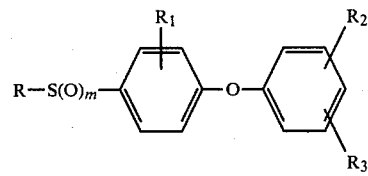

wherein m represents the integer 0, 1 or 2; R represents trihalomethyl, alkyl or phenyl; $R_1$ represents hydrogen, bromo, chloro, fluoro, cyano, nitro, amino, alkyl, alkoxy or trifluoromethyl; $R_2$ represents hydroxyl, bromo, chloro, fluoro, cyano, acetyl, benzoyl, substituted benzoyl, alkyl, alkoxy, substituted alkoxy, benzyl, substituted benzyl, alkylthio, alkylsulfinyl, alkylsulfonyl, alkylaminosulfonyl, dialkylaminosulfonyl, or the radical $-O(CH_2)_nR_4$ wherein n represents the integer 1, 2 or 3 and $R_4$ represents cyano or dialkylamino; $R_3$ represents hydrogen, hydroxyl, bromo, chloro, fluoro, cyano, acetyl, benzoyl, substituted benzoyl, alkyl, alkoxy, substituted alkoxy, benzyl, substituted benzyl, alkylthio, alkylsulfinyl, alkylsulfonyl, alkylaminosulfonyl, dialkylaminosulfonyl, or the radical $-O(CH_2)_nR_4$ wherein n represents the integer 1, 2 or 3; and $R_4$ represents cyano or dialkylamino; or alternatively $R_2$ and $R_3$ taken together represent the radical $-O-C(X)_2-O-$ wherein X represents hydrogen, bromo, chloro or fluoro.

Methods of using the above-noted compounds and structurally related compounds to employ their antiviral activity are also disclosed as well as pharmaceutically-acceptable compositions.

39 Claims, No Drawings

SULFUR-SUBSTITUTED DIPHENYL ETHERS HAVING ANTIVIRAL ACTIVITY

BACKGROUND OF THE INVENTION

Various sulfur-substituted diphenyl ethers are known in the literature, as for example, those compounds found in U.S. Pat. No. 3,813,444 and *Chem. Abstracts* 67:116462q. The majority of the literature compounds are utilized for agricultural purposes.

SUMMARY OF THE INVENTION

The present invention is directed to a compound corresponding to the formula:

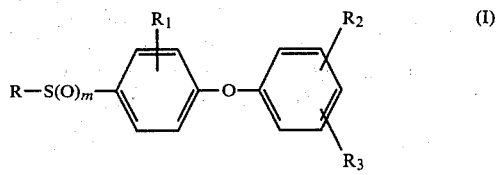

wherein m represents the integer 0, 1 or 2; R represents trihalomethyl, alkyl or phenyl; $R_1$ represents hydrogen, bromo, chloro, fluoro, cyano, nitro, amino, alkyl, alkoxy or trifluoromethyl; $R_2$ represents hydroxyl, bromo, chloro, fluoro, cyano, acetyl, benzoyl, substituted benzoyl, alkyl, alkoxy, substituted alkoxy, benzyl, substituted benzyl, alkylthio, alkylsulfinyl, alkylsulfonyl, alkylaminosulfonyl, dialkylaminosulfonyl, or the radical —O(CH$_2$)$_n$R$_4$ wherein n represents the integer 1, 2 or 3; and R$_4$ represents cyano or dialkylamino; R$_3$ represents hydrogen, hydroxyl, bromo, chloro, fluoro, cyano, acetyl, benzoyl, substituted benzoyl, alkyl, alkoxy, substituted alkoxy, benzyl, substituted benzyl, alkylthio, alkylsulfinyl, alkylsulfonyl, alkylaminosulfonyl, dialkylaminosulfonyl, or the radical —O(CH$_2$)$_n$R$_4$ wherein n represents the integer 1, 2 or 3; and R$_4$ represents cyano or dialkylamino; or alternatively R$_2$ and R$_3$ taken together represent the radical —O—C(X)$_2$—O— wherein X represents hydrogen, bromo, chloro or fluoro.

The compounds disclosed herein exhibit antiviral activity and thus can be used to inhibit viral replication by contacting a virus and preferably, virus host cells with an effective virus inhibiting amount of one or more of the subject compounds. The present invention is further directed to methods of using compounds of the formula:

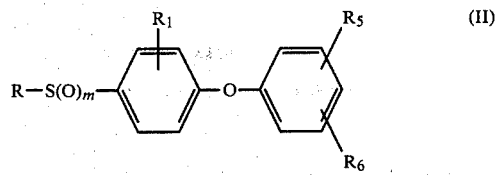

wherein m, R and R$_1$ have the same meanings as defined with regard to formula I; and R$_5$ and R$_6$ each independently represent hydrogen, nitro, hydroxyl, bromo, chloro, fluoro, cyano, acetyl, benzoyl, substituted benzoyl, alkyl, alkoxy, substituted alkoxy, benzyl, substituted benzyl, alkylthio, alkylsulfinyl, alkylsulfonyl, alkylaminosulfonyl, dialkylaminosulfonyl, or the radical —O(CH$_2$)$_n$R$_4$ wherein n and R$_4$ have the same meanings as defined with regard to formula I; or alternatively R$_5$ and R$_6$ taken together represent the radical —O—C(X$_2$)—O— wherein X represents hydrogen, bromo, chloro or fluoro; wherein the compounds represented by formula II are antiviral agents in which a virus or virus host cell (that is, a cell susceptible to infection by the virus) is contacted with an effective amount of one or more of such compounds.

The present invention is also directed to antiviral compositions which can contain from about 0.00001 percent (%) or less to about 99% by weight of the active compound in combination with a pharmaceutically-acceptable carrier. Typically, in those combinations employing a low percentage of active compound, the pharmaceutically-acceptable carrier is in liquid form, therefore a composition containing 0.00001% or less by weight of active compound is equivalent to a composition containing about 0.1 microgram (μg) or less of the active compound per milliliter (ml) of carrier.

As used in the specification and claims, the term "trihalomethyl" refers to a trisubstituted methyl group with the substituents selected from bromo, chloro or fluoro, as for example, trifluoromethyl, trichloromethyl and chlorodifluoromethyl;

"alkyl" refers to an alkyl group having from 1 to 3 carbon atoms such as methyl, ethyl, propyl and isopropyl;

"alkoxy" refers to an alkoxy group having from 1 to 3 carbon atoms such as methoxy, ethoxy, propoxy and isopropoxy;

"substituted alkoxy" refers to an alkoxy group substituted with one or more substituents selected from bromo, chloro or fluoro such as 2,2-dichloro-1,1-difluoroethoxy;

"substituted benzoyl" refers to a benzoyl radical in which the benzene ring is substituted with one to five substituents selected from bromo, chloro, fluoro, methyl or methoxy;

"substituted benzyl" refers to a benzyl radical in which the benzene ring is substituted with one to five substituents selected from bromo, chloro, fluoro, methyl or methoxy;

those substituents which incorporate the term "alkyl" refer to groups in which the alkyl portion has from 1 to 3 carbon atoms, thus, for example, "alkylsulfonyl" refers to methylsulfonyl, ethylsulfonyl, propylsulfonyl and isopropylsulfonyl and "dialkylaminosulfonyl" represents, for example, dimethylaminosulfonyl, diethylaminosulfonyl, dipropylaminosulfonyl, diisopropylaminosulfonyl, N,N-methylethylaminosulfonyl, and the like.

For convenience, the compounds represented by formula I and formula II are often referred to herein as "subject compounds", it being understood that information pertaining to compound activity, preparation, use, etc. is applicable to the compounds of both formula I and formula II unless reference is made specifically to either the formula I compounds or the formula II compounds.

Preferred subject compounds for antiviral use are those compounds in which R$_2$ and R$_3$ are other than hydroxy, substituted alkoxy, or the radical —O(CH$_2$)$_n$R$_4$ wherein n represents the integer 1, 2 or 3; and R$_4$ represents cyano or dialkylamino.

Also preferred are those subject compounds in which m represents the integer 0, 1 or 2; R represents trifluoromethyl, methyl or phenyl; R$_1$ represents hydrogen; R$_2$ (in the case of formula I compounds) or R$_5$ (in the case of formula II compounds) represents bromo or chloro;

and $R_3$ (in the case of formula I compounds) or $R_6$ (in the case of formula II compounds) represents hydrogen, bromo or chloro.

Those subject compounds in which m represents the integer 0, 1 or 2; R represents methyl; $R_1$ represents hydrogen; $R_2$ (in the case of formula I compounds) or $R_5$ (in the case of formula II compounds) represents bromo or chloro; and $R_3$ (in the case of formula I compounds) or $R_6$ (in the case of formula II compounds) represents hydrogen, bromo or chloro; are especially preferred.

In general, the subject compounds are solids which are soluble to varying degrees in organic solvents such as methylene chloride, methanol and ethanol.

The difference between formula II and formula I is that $R_5$ and $R_6$ of formula II include substituents which are not included in the definition of $R_2$ and $R_3$ with regard to formula I. Because of the broader definition of $R_5$ and $R_6$, the compounds represented by formula II include several compounds known in the art, whereas such compounds are not included among the compounds corresponding to formula I. For example, some of the compounds corresponding to formula II in which m represents the integer 0, 1 or 2; R represents alkyl; $R_1$ represents hydrogen, chloro or methyl; $R_5$ represents nitro; and $R_6$ represents hydrogen or nitro have either been prepared or are disclosed in the art (see U.S. Pat. No. 3,813,444 and *Chem. Abstracts* 67:116462 q). Both formula I compounds and formula II compounds can be prepared employing the procedures described herein.

DETAILED DESCRIPTION OF THE INVENTION

The subject compounds are prepared by reacting a substituted benzene compound of the formula Bz-A with a substituted benzene compound of the formula Bz'—O—Y, wherein A represents bromo, chloro, fluoro or iodo; Y represents hydrogen or a phenate salt forming cation such as sodium or potassium, Bz represents one of the moieties

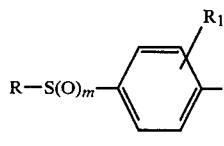

or

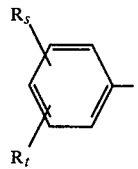

(wherein m, R and $R_1$ have the same meanings as previously defined herein) and Bz' represents the other of said moieties.

In the above formula, $R_s$ represents $R_2$ or $R_5$; and $R_t$ represents $R_3$ or $R_6$ with the proviso that when $R_s$ is $R_2$ then $R_t$ is $R_3$, and when $R_s$ is $R_5$ then $R_t$ is $R_6$. The substituents $R_2$, $R_3$, $R_5$ and $R_6$ have the same meanings as previously defined herein. Therefore in those situations in which $R_s$ and $R_t$ are employed herein, the preparation of the appropriate formula I compound is readily apparent by understanding that $R_s$ represents $R_2$; and $R_t$ represents $R_3$. Whereas, the various formula II compounds are prepared employing the same conditions, except in the case of the formula II compounds, $R_s$ represents $R_5$; and $R_t$ represents $R_6$.

The reaction proceeds when the reactants are contacted and mixed, in the presence of phenate salt forming alkali such as an alkali metal hydroxide or carbonate when Y is hydrogen, and in the presence of an inert organic solvent such as dimethyl sulfoxide (DMSO), tetramethylsulfone (sulfolane), hexamethyl phosphoramide, acetonitrile or methylene chloride. The reactants can be combined in any order and in various proportions, however, the reactants are consumed in equimolar proportions and the use of approximately equimolar proportions is preferred. When Y is hydrogen, an approximately equimolar amount of phenate forming alkali is also employed. The compounds can be separated and purified by conventional procedures.

The compounds of the present invention are conveniently prepared by reacting a compound of the formula:

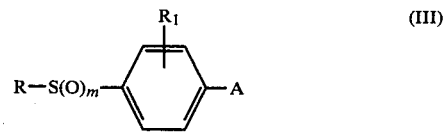 (III)

with a compound of the formula

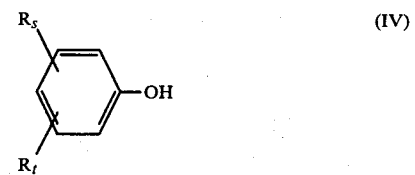 (IV)

wherein m, A, R, $R_1$, $R_s$ and $R_t$ have the same meanings as previously defined herein, in an inert organic solvent in the presence of an alkaline agent (also referred to herein as a "phenate salt forming alkali") under conditions at which the subject compound is formed. The alkaline agent should be of sufficient basicity and in sufficient concentration to convert the compound of formula IV to its appropriate salt for reaction with the compound of formula III.

Alternatively, the subject compounds can be prepared by reacting a compound of the formula

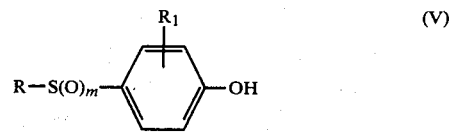 (V)

with a substituted halobenzene of the formula

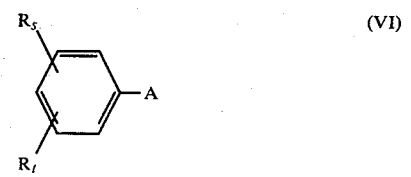 (VI)

wherein m, R, $R_1$, $R_s$, $R_t$ and A have the same definitions as previously defined herein. The reaction proceeds when the reactants are contacted and mixed in an inert organic solvent in the presence of an alkaline agent under conditions sufficient to form the subject compound. The alkaline agent should be of sufficient basicity and in sufficient concentration to convert the compound of formula V to its salt for reaction with the compound of formula VI. Depending upon the substituents in the compound of formula VI, more severe reaction conditions can be required than for the reaction of the compound of formula III with the compound of formula IV, and/or the reaction can produce more than one of the subject compounds, requiring additional separation steps when a single subject compound is desired.

In particular, subject compounds can be prepared by at least one of the following methods:

METHOD I

The compound represented by formula III, in which A is generally chloro or fluoro, is reacted with the compound represented by formula IV. Reaction is accomplished when approximately equimolar concentrations of the above-noted reactants are contacted and mixed in an inert organic solvent, preferably dimethyl sulfoxide or sulfolane and heated at a temperature of from about 50° C. to 250° C. in the presence of an alkaline agent, preferably sodium hydroxide or potassium carbonate for a time sufficient to obtain the desired subject compound. Usually a reaction time of about 30 minutes to about 10 hours is sufficient. The choice of reaction temperature can dictate which inert organic solvent is to be employed for the preparation of particular subject compounds i.e., higher boiling solvents should be used at the higher temperatures. Traditional methods, such as dilution with water and filtration, well known in the art can be employed to recover the subject compound from the reaction mixture. Purification is accomplished by conventional techniques such as column chromatography and/or recrystallization from solvents such as methanol, ethanol, 2-propanol, ethyl acetate, chloroform, hexane and the like.

METHOD II

The compound represented by formula VI in which A is generally chloro or fluoro is reacted with the compound represented by formula V. The reaction proceeds when approximately equimolar concentrations of the above-noted reactants are contacted and mixed in an inert organic solvent, preferably dimethyl sulfoxide or sulfolane and heated at a temperature from about 75° C. to 250° C. in the presence of an alkaline agent, preferably sodium hydroxide or potassium carbonate for a time sufficient to obtain the desired subject compound. Usually a reaction time of from about 2 hours to about 12 hours is sufficient. The choice of reaction temperature can dictate which inert organic solvent is used for the above reaction.

Subject compounds are recovered from the reaction mixture and purified utilizing procedures essentially the same as those described hereinabove.

Although the subject compounds can be prepared by the above-noted procedures, further alternate synthesis routes can often be conveniently employed and in some instances may be the preferred method of preparation. Several of these alternate synthesis routes are as follows:

The compounds represented by formula I or formula II, prepared by one of the above-noted reactions, can undergo subsequent reactions to form other subject compounds.

METHOD III

For example, the compound 1-(4-methylsulfonyl)-phenoxy)benzene, conveniently formed from 4-chlorophenyl methyl sulfone and phenol under the conditions described above, is reacted with chlorosulfonic acid under conditions suitable for the formation of 4-(4-(methylsulfonyl)phenoxy)benzenesulfonyl chloride. Generally a temperature of from about 0° C. to 75° C. with reaction periods which range from virtually instantaneous reaction to about a few minutes to about 1 hour are sufficient. The 4-(4-(methylsulfonyl)phenoxy)-benzenesulfonyl chloride is dissolved in methylene chloride and an aqueous solution of an alkylamine or dialkylamine added slowly thereto. By preselecting the appropriate alkylamine or dialkylamine, some of the subject compounds having alkylaminosulfonyl or dialkylaminosulfonyl substituents can be prepared employing essentially the same procedure.

METHOD IV

In addition, various subject compounds wherein m represents the integer 0 can be oxidized to those subject compounds in which m represents the integer 1 (sulfoxides) or the integer 2 (sulfones). Such oxidation is conveniently accomplished utilizing suitable oxidizing agents as, for example, glacial acetic acid and hydrogen peroxide; or 3-chloroperbenzoic acid, employing reaction conditions well known in the art.

For those subject compounds containing more than one sulfur atom the above oxidation reactions can still prove useful since the oxidation states of the sulfur can be controlled by preselecting the points in the synthetic process at which the particular sulfur containing substituents are added and the point and conditions at which the oxidation reaction(s) are performed.

METHOD V

A compound of formula II such as, for example, 1-(4-(methylsulfonyl)phenoxy]benzene, can undergo a Friedel-Crafts acylation utilizing the following procecure: Approximately equimolar quantities of the above phenoxybenzene and an acyl halide, such as acetyl chloride, benzoyl chloride or substituted benzoyl chloride, are contacted and mixed in methylene chloride in the presence of about an equimolar concentration of AlCl$_3$. The reaction proceeds at a temperature from about 20° C. to reflux temperature (~40° C.) until the acylated compound is obtained. Generally a reaction time of about ½ hour to about 2 hours is sufficient.

METHOD VI

Still other subject compounds can be prepared utilizing procedures in which various substituents are altered or replaced. For example, a nitro substituent can be changed to an amino substituent by employing a reductive amination under pressure in the presence of a noble metal catalyst such as palladium. This reaction is exemplified herein by the reductive amination of 4-(4-(methylsulfonyl)-2-nitrophenoxy)-1,2-dichlorobenzene to obtain 2-(3,4-dichlorophenoxy)-5-(methylsulfonyl)benzenamine.

METHOD VII

A compound such as 2-(3,4-dichlorophenoxy)-5-(methylsulfonyl)benzenmine can be utilized to prepare a diazonium salt and the resulting diazonium salt converted to various subject compounds. For example, the diazonium salt (corresponding to formula I where $R_1$ is a diazonium salt, i.e., $-N_2^+X^-$, in which $X^-$ is a suitable anion such as halide or bisulfate, instead of the above defined $R_1$ moieties; and m, R, $R_2$ and $R_3$ have the same meanings as defined with regard to formula I) can be used to obtain a subject compound containing a cyano substituent. Such procedures are well known in the art and are illustrated in the examples herein concerning the conversion of 2-(3,4-dichlorophenoxy)-5-(methylsulfonyl)benzenamine to 2-(3,4-dichlorophenoxy)-5-(methylsulfonyl)benzonitrile via the diazonium salt intermediate.

METHOD VIII

A subject compound such as, for example, 4-(4-(methylsulfonyl)phenoxy)-1-methoxybenzene can be converted to 4-(4-(methylsulfonyl)phenoxy)phenol using conventional methodology as illustrated in Example 21. The 4-(4-(methylsulfonyl)phenoxy)phenol can then be employed to make subject compounds in which $R_s$ or $R_t$ are various oxygen-containing substituents.

As used in the specification and claims, the term "inert organic solvent" refers to organic solvents which do not undergo reaction themselves under the conditions employed for making the subject compounds. Examples of suitable inert organic solvents are dimethyl sulfoxide, dimethylformamide, acetonitrile, methylene chloride, sulfolane and hexamethyl phosphoramide.

The following examples are included to further illustrate the invention but are not to be contrued as a limitation thereon.

EXAMPLE 1

4-(4-(Methylsulfonyl)phenoxy)-1,2-dichlorobenzene

To a solution of 9.40 grams (g) (0.0576 mole) of 3,4-dichlorophenol dissolved in 150 milliliters (ml) of dimethyl sulfoxide (DMSO) was added 2.30 g (0.0576 mole) of sodium hydroxide (NaOH). The mixture was heated to 60° C. and 10.0 g (0.0524 mole) of 4-chlorophenyl methyl sulfone was added. The reaction mixture was heated at 165° C. for 2.5 hours (hrs) and cooled. The mixture was poured into water and the crystalline product collected by filtration, washed well with water and dried, which gave 12.8 g (77.1% yield) of product. Recrystallization from ethanol afforded purified 4-(4-(methylsulfonyl)phenoxy)-1,2-dichlorobenzene, melting at a melting point (mp) of 124.5°-125.5° C.

EXAMPLE 2

4-(4-(Methylsulfonyl)phenoxy)-1-chlorobenzene

To a solution of 7.41 g (0.0576 mole) of 4-chlorophenol dissolved in 150 ml of DMSO was added 2.30 g (0.0576 mole) of NaOH. The mixture was heated to 60° C. and 10.0 g (0.0524 mole) of 4-chlorophenyl methyl sulfone was added. The reaction mixture was heated at 160° C. for 3 hrs and cooled. The mixture was poured into a solution of 400 ml of 2 Normal (N) aqueous NaOH and 300 ml of water. The crystalline product was collected by filtration, washed well with water, and dried, which gave 13.8 g (93.2% yield) of product, m.p. 109°-111° C. Recrystallization from ethanol afforded purified 4-(4-(methylsulfonyl)phenoxy)-1-chlorobenzene, mp 111°-112° C.

EXAMPLE 3

1-(4-(4-(Methylsulfonyl)phenoxy)phenyl)ethanone

To a solution of 20.7 g (0.220 mole) of phenol dissolved in 250 ml of DMSO was added 8.80 g (0.0220 mole) of NaOH. The mixture was heated to 60° C. and 38.1 g (0.200 mole) of 4-chlorophenyl methyl sulfone was added. The reaction mixture was heated at 160° C. for 3 hrs and cooled. The mixture was poured into a solution of 400 ml of 2 N aqueous NaOH and 300 ml of water. The crystalline product was collected by filtration, washed well with water and dried, which gave 48.6 g (98% yield) of product. Recrystallization from ethanol afforded purified, 1-(4-(methylsulfonyl)phenoxy)benzene, mp 84°-85.5° C.

To a solution of 5.0 g (0.0202 mole) of 1-(4-(methylsulfonyl)phenoxy)benzene and 2.20 g (0.0280 mole) of acetyl chloride dissolved in 35 ml of methylene chloride ($CH_2Cl_2$) was slowly added 6.70 g (0.0503 mole) of anhydrous aluminum chloride. The mixture was heated at reflux for 45 minutes, cooled and poured over ice and concentrated hydrochloric acid (conc. HCl). Additional $CH_2Cl_2$ was added and the organic layer separated, washed with water and dried ($Na_2SO_4$). Removal of solvent in vacuo yielded 5.2 g (88.9% yield) of purified 1-(4-(4-(methylsulfonyl)phenoxy)phenyl)ethanone, mp 131°-132.5° C.

EXAMPLE 4

(4-(4-(Methylsulfonyl)phenoxy)phenyl)phenylmethanone

To a solution of 5.0 g (0.0202 mole) of 1-(4-(methylsulfonyl)phenoxy)benzene and 6.70 g (0.0503 mole) of anhydrous aluminum chloride dissolved in 60 ml of $CH_2Cl_2$ was added 3.72 g (0.0264 mole) of benzoyl chloride. The reaction mixture was heated at reflux for 45 minutes, cooled and poured over ice and conc. HCl. Additional $CH_2Cl_2$ was added and the organic layer separated, washed with water and dried ($Na_2SO_4$). Removal of solvent in vacuo afforded product and unreacted benzoyl chloride. The mixture was slurried in refluxing water for 30 minutes to hydrolyze the unreacted benzoyl chloride. The product was collected by filtration, washed with water and dried, which gave 6.68 g (94.75% yield) of product. Recrystallization from ethanol afforded purified (4-(4-(methylsulfonyl)phenoxy)phenyl)phenylmethanone, mp 164°-165° C.

EXAMPLE 5

4-(4-(Methylthio)phenoxy)benzonitrile

A mixture of 12.1 g (0.100 mole) of 4-fluorobenzonitrile, 21.0 g (0.150 mole) of 4-(methylthio)phenol, 20.7 g (0.150 mole) of anhydrous potassium carbonate ($K_2CO_3$) and 150 ml of hexamethyl phosphoramide was heated at 100° C. for 4 hrs. The reaction mixture was cooled and poured into a solution of 200 ml of 20% aqueous NaOH and 500 ml of water. The crystalline product was collected by filtration and washed well with water. The product was dissolved in $CH_2Cl_2$ and dried ($Na_2SO_4$). Removal of solvent in vacuo afforded 11.3 g (46.9% yield) of product. Recrystallization from hexane gave purified 4-(4-(methylthio)phenoxy)benzonitrile, mp 65°-66° C.

EXAMPLE 6

1,2-Dichloro-4-(4-(methylsulfinyl)phenoxy)benzene

A mixture of 16.14 g (0.102 mole) of 4-fluorophenyl methyl sulfoxide, 33.18 g (0.204 mole) of 3,4-dichlorophenol, 28.15 g (0.204 mole) of anhydrous $K_2CO_3$ and 150 ml of sulfolane was heated at 170° C. for 4 hrs and cooled. The reaction mixture was poured into a solution of 20% aqueous NaOH and 500 ml of water. The homogeneous solution was extracted with diethyl ether. The organic layer was washed with water, dried ($Na_2SO_4$) and solvent removed in vacuo leaving 24.5 g (79.8% yield) of product. Recrystallization from ethanol followed by column chromatography using silica gel as the support and chloroform as the eluent afforded purified 1,2-dichloro-4-(4-(methylsulfinyl)phenoxy)benzene, mp 92°–93.5° C.

EXAMPLE 7

4-(4-(Methylsulfinyl)phenoxy)benzonitrile

To a solution of 4.6 g (0.0191 mole) of 4-(4-(methylthio)phenoxy)benzonitrile dissolved in 50 ml of glacial acetic acid was added dropwise 2.38 g (0.0210 mole) of 30% aqueous hydrogen peroxide. The mixture was heated at 50° C. for 1 hr and most of the solvent removed in vacuo. The crude product was dissolved in $CH_2Cl_2$ and washed with 2 N aqueous NaOH and water. The organic layer was dried ($Na_2SO_4$) and solvent removed in vacuo leaving 4.7 g (95.9% yield) of 4-(4-(methylsulfinyl)phenoxy)benzonitrile as an oil.

EXAMPLE 8

4-(4-(Methylsulfonyl)phenoxy)benzonitrile

A mixture of 5.23 g (0.0300 mole) of 4-fluorophenyl methyl sulfone, 7.15 g (0.0600 mole) of 4-cyanophenol, 8.29 g (0.0600 mole) of anhydrous $K_2CO_3$ and 90 ml of sulfolane was heated at 150° C. for 3.5 hrs. The mixture was cooled and poured into a solution of 100 ml of 20% aqueous NaOH and 500 ml of water. Extraction of the basic solution with diethyl ether afforded 2.3 g (28% yield) of product after removal of solvent in vacuo. The product was purified by column chromatography using silica gel as the support and chloroform as the eluent. The purified 4-(4-(methylsulfonyl)phenoxy)benzonitrile was found to have a melting point of 127°–128.5° C.

EXAMPLE 9

1-Bromo-4-(4-methylsulfonyl)phenoxy)benzene

A mixture of 9.54 g (0.0500 mole) of 4-chlorophenyl methyl sulfone, 13.0 g (0.0750 mole) of 4-bromophenol, 10.37 g (0.0750 mole) of $K_2CO_3$ and 150 ml of sulfolane was heated at 150° C. for 5.5 hrs and at 160° C. for 3.5 hrs. The reaction mixture was cooled and poured into a solution of 200 ml of 20% aqueous NaOH and 400 ml of water. The crystalline product was collected by filtration, washed well with water and dried, which gave 8.27 g (50.6% yield) of product. Recrystallization from ethanol afforded purified 1-bromo-4-(4-methylsulfonyl)phenoxy)benzene, mp 127.5°–129° C.

EXAMPLE 10

4-(4-(Phenylsulfonyl)phenoxy)-1,2-dichlorobenzene

To a solution of 9.0 g (0.0550 mole) of 3,4-dichlorophenol dissolved in 150 ml of DMSO was added 2.20 g (0.0550 mole) of NaOH. The mixture was heated to 60° C. and 12.5 g (0.0529 mole) of 4-fluorophenyl phenyl sulfone was added. The reaction mixture was heated at 125° C. for 3.25 hrs and cooled. The mixture was poured into a solution of 100 ml of 20% aqueous NaOH and 600 ml of water. The crystalline product was collected by filtration, washed well with water and partially dried. Recrystallization from ethanol afforded 16.9 g (84.5% yield) of purified 4-(4-(phenylsulfonyl)phenoxy)-1,2-dichlorobenzene, mp 145°–146° C.

EXAMPLE 11

N,N-Dimethyl-4-(4-(phenylsulfonyl)phenoxy)benzenesulfonamide

To a solution of 6.60 g (0.0330 mole) of N,N-dimethyl-4-hydroxybenzenesulfonamide dissolved in 150 ml of DMSO was added 1.32 g (0.0330 mole) of NaOH. The mixture was heated at 60° C. for 10 minutes and 7.1 g (0.030 mole) of 4-fluorophenyl phenyl sulfone was added. The reaction mixture was heated at 100° C. for 3 hrs and at 125° C. for 3 hrs and cooled. The mixture was poured into a solution of 200 ml of 20% aqueous NaOH and 500 ml of water. The crystalline product was collected, washed well with water and dried, which gave 11.5 g (92% yield) of product. Recrystallization from aqueous DMSO followed by recrystallization from ethanol afforded purified N,N-dimethyl-4-(4-(phenylsulfonyl)phenoxy)benzenesulfonamide, mp 99°–100° C.

EXAMPLE 12

N,N-Dimethyl-4-(4-(methylsulfonyl)phenoxy)benzenesulfonamide

To 15 ml (0.227 mole) of chlorosulfonic acid was added 10.0 g (0.0403 mole) of 1-(4-(methylsulfonyl)phenoxy)benzene in small portions keeping the temperature below 55° C. After the addition was complete and the mixture had stirred at ambient temperature for 10 minutes, the mixture was slowly poured over ice and water. The crystalline 4-(4-(methylsulfonyl)phenoxy)benzenesulfonyl chloride was collected by filtration, washed with water and dried. The material was dissolved in 350 ml of $CH_2Cl_2$ and 26.6 g (0.177 mole) of 30% aqueous dimethylamine was added dropwise. The reaction mixture was heated at reflux temperature for 1.5 hrs and cooled. The mixture was extracted with 3 N aqueous hydrogen chloride, dried ($Na_2SO_4$) and solvent removed in vacuo, which gave 13.4 g (93.7% yield) of product. Recrystallization from ethanol, followed by purification using column chromatography with silica gel as the support and chloroform as the eluent gave purified N,N-dimethyl-4-(4-(methylsulfonyl)phenoxy)benzenesulfonamide, mp 127.5°–130° C.

EXAMPLE 13

N,N-Diethyl-4-(4-(methylsulfonyl)phenoxy)benzenesulfonamide, mp 101°–103.5° C.

N,N-Diethyl-4-(4-methylsulfonyl)phenoxy)benzenesulfonamide was prepared (83.1% yield) utilizing essentially the same procedure as that described in Example 12.

EXAMPLE 14

4-(2-Chloro-4-(methylsulfonyl)phenoxy)-1,2-dichlorobenzene

To a solution of 9.09 g (0.0558 mole) of 3,4-dichlorophenol dissolved in 150 ml of DMSO was added 2.23 g (0.0558 mole) of NaOH. The mixture was heated to 60° C. and 11.3 g (0.0502 mole) of 3,4-dichlorophenyl methyl sulfone was added and the mixture heated at 150° C. for 3.75 hrs. The mixture was cooled and poured into water. The crystalline product was collected by filtration, washed with water and dried, which gave 14.5 g (82.4% yield) of product. Recrystallization from ethanol afforded purified 4-(2-chloro-4-(methylsulfonyl)phenoxy)-1,2-dichlorobenzene, mp 102°-104° C.

EXAMPLE 15

4-(4-(Methylsulfonyl)-2-nitrophenoxy)-1,2-dichlorobenzene, mp 173°-174° C.

The compound 4-(4-(methylsulfonyl)-2-nitrophenoxy)-1,2-dichlorobenzene was prepared (88% yield) utilizing essentially the same procedure as described in Example 1 and purified by recrystallization from chloroform.

EXAMPLE 16

2-(3,4-Dichlorophenoxy)-5-(methylsulfonyl)benzenamine

A slurry of 10.5 g (0.0290 mole) of 4-(4-(methylsulfonyl)-2-nitrophenoxy)-1,2-dichlorobenzene and 350 ml of glacial acetic acid was placed in a Parr bottle and 0.5 g of 5% palladium on carbon added under nitrogen. The mixture was placed on a Parr hydrogenator apparatus and the desired reduction carried out with 50 pounds per square inch (psi) of hydrogen. Two batches of equal size were run and the catalyst removed by filtration. The solvent was removed in vacuo leaving crude product which was slurried in aqueous NaOH to remove any residual acetic acid. The aqueous layer was decanted from the product which was dried, to obtain 14.4 g (74.8% yield) of product. Recrystallization from ethanol and water afforded purified 2-(3,4-dichlorophenoxy)-5-(methylsulfonyl)benzenamine, mp 119°-121° C.

EXAMPLE 17

2-(3,4-Dichlorophenoxy)-5-(methylsulfonyl)benzonitrile

A mixture of 5.0 g (0.0151 mole) of 2-(3,4-dichlorophenoxy)-5-(methylsulfonyl)benzenamine (Example 16), 75 ml of glacial acetic acid, 37.5 ml of water and 3.0 g (0.0306 mole) of concentrated sulfuric acid was cooled to 0° C. and 1.5 g (0.0217 mole) of sodium nitrite dissolved in 15 ml of water was added slowly. The mixture was stirred at 0° C. for 20 minutes and then added slowly to a mixture of 7.5 g (0.0838 mole) of cuprous cyanide and 30 g (0.612 mole) of sodium cyanide dissolved in 150 ml of water at 0° C. The mixture was stirred at 0° C. for 45 minutes and allowed to warm to room temperature. The mixture was then heated at 50° C. for 1 hr. The mixture was poured into water and the crystalline product collected by filtration, washed with water and dried, to obtain 4.95 g (96.1% yield) of product. Purification was accomplished by column chromatography using silica gel as the support and chloroform as the eluent followed by recrystallization from ethyl acetate, which gave purified 2-(3,4-dichlorophenoxy)-5-(methylsulfonyl)benzonitrile, mp 162°-163° C.

EXAMPLE 18

4-(4-(Methylsulfonyl)phenoxy)-1-methoxybenzene

To a solution of 38.1 g of 4-chlorophenyl methyl sulfone and 37.2 g of 4-methoxyphenol dissolved in 150 ml of sulfolane was added 41.5 g of $K_2CO_3$. The mixture was heated at 160° C. for 7 hrs and then at 170° C. for 14.5 hrs and cooled. The mixture was poured into aqueous NaOH and the crystalline product collected by filtration, washed well with water and dried, which gave 47.5 g (85.3% yield) of product. Recrystallization from ethanol gave purified 4-(4-(methylsulfonyl)phenoxy)-1-methoxybenzene, mp 151.5°-153° C.

EXAMPLE 19

4-(3-Methyl-4-(methylsulfonyl)phenoxy)-1,2-dichlorobenzene

A slurry of 6.14 g of 4-chloro-2-methylphenyl methyl sulfone, 8.35 g of 3,4-dichlorophenol and 7.08 g of $K_2CO_3$ in 150 ml of sulfolane was heated at 170° C. for 7 hrs. The product (6.3 g, 63.4% yield) was isolated from the reaction mixture essentially as described in Example 18. Recrystallization from ethanol afforded purified 4-(3-methyl-4-(methylsulfonyl)phenoxy)-1,2-dichlorobenzene, mp 154°-156° C.

EXAMPLE 20

1-(4-Methylsulfonyl)phenoxy)-4-(phenylmethyl)benzene

A slurry of 5.72 g of 4-chlorophenyl methyl sulfone, 6.08 g of 4-benzylphenol and 4.56 g of $K_2CO_3$ in 150 ml of DMSO was heated at 160° C. for 8.5 hrs. The product (9.55 g, 94.1% yield) was recovered from the reaction mixture essentially as described in Example 18. Recrystallization from 2-propanol and then from aqueous acetic acid afforded purified 1-(4-(methylsulfonyl)phenoxy)-4-(phenylmethyl)benzene, mp 109°-110° C.

EXAMPLE 21

4-(4-(Methylsulfonyl)phenoxy)phenol

A solution of 37.3 g of 4-(4-(methylsulfonyl)phenoxy)-1-methoxybenzene (Example 18), 41 ml of 48% aqueous hydrogen bromide and 185 ml of glacial acetic acid was heated at reflux under nitrogen for 21 hrs. The reaction mixture was cooled and the solvent removed in vacuo. The product was collected by filtration, washed well with water and dried, which gave 35.0 g (98.9% yield) of the product. Recrystallization from aqueous ethanol gave purified 4-(4-(methylsulfonyl)phenoxy)phenol, mp 129°-130° C.

EXAMPLE 22

1-(2,2-Dichloro-1,1-difluoroethoxy)-4-(4-(methylsulfonyl)phenoxy)benzene

To a solution of 5.29 g (0.0200 mole) of 4-(4-(methylsulfonyl)phenoxy)phenol (Example 21) in 100 ml of acetonitrile was added 0.80 g (0.0200 mole) of NaOH. The mixture was stirred at room temperature for 1 hr and then cooled to 3° C. in an ice bath. To the cold slurry was slowly added 4.0 g (0.0300 mole) of 1,1-difluoro-2,2-dichloroethylene dissolved in 15 ml of acetonitrile and the reaction mixture stirred at 3°-5° C. for 3 hrs. To the cold mixture 150 ml of water was added which resulted in the product precipitating as an oil. The product was extracted from the mixture with $CH_2Cl_2$. The organic layer was washed with water, dried ($Na_2SO_4$) and solvent rmoved in vacuo, which gave 7.1 g (89.4% yield) of product. Purification was accomplished by column chromatography using silica gel as the support and chloroform as the eluent, which afforded purified 1-(2,2-dichloro-1,1-difluoroethoxy)-4-(4-(methylsulfonyl)phenoxy)benzene, mp 67°–70° C.

EXAMPLE 23

4-(4-Methylsulfonyl)phenoxy)phenoxy)acetonitrile

To a solution of 5.29 g (0.0200 mole) of 4-(4-(methylsulfonyl)phenoxy)phenol and 1.51 g (0.0200 mole) of 2-chloroacetonitrile in 100 ml of acetonitrile was added 3.0 g (0.0220 mole) of $K_2CO_3$. The mixture was heated at reflux for 3.5 hrs and cooled. The mixture was poured into aqueous NaOH and the product extracted from the mixture with $CH_2Cl_2$. The organic layer was extracted with aqueous NaOH, water and dried ($Na_2SO_4$). Removal of solvent in vacuo afforded 5.6 g (92.4% yield) of product. Recrystallization from ethanol followed by washing with aqueous NaOH and water afforded purified (4-(4-(methylsulfonyl)phenoxy)phenoxy)acetonitrile, mp 114°–115.5° C.

EXAMPLE 24

N,N-Diethyl-2-(4-(4-(methylsulfonyl)phenoxy)phenoxy)ethylamine

To a solution of 7.93 g (0.0300 mole) of 4-(4-methylsulfonyl)phenoxy)phenol in 75 ml of $CH_2Cl_2$ was added 75 ml of 50% aqueous NaOH. To this mixture was added 0.50 g of benzyltriethylammonium chloride and 10.3 g (0.0600 mole) of diethylaminoethyl chloride hydrochloride. The mixture was heated at reflux for 3.25 hrs and cooled. To the mixture was added 150 ml of $CH_2Cl_2$ and 100 ml of water. The organic layer was separated, washed with water and dried ($Na_2SO_4$). Removal of solvent in vacuo gave 10.1 g (92.7% yield) of product. Recrystallization from ethanol followed by column chromatography on silica gel using a solution of 2% methanol and 98% chloroform as the eluent gave purified N,N-diethyl-2-(4-(4-methylsulfonyl)phenoxy)-phenoxy)ethylamine, mp 92.5°–94° C.

EXAMPLE 25

4-(4-((Trifluoromethyl)sulfonyl)phenoxy)-1,2-dichlorobenzene

To a solution of 4.7 g (0.0192 mole) of 4-chlorophenyl trifluoromethyl sulfone prepared according to known procedures (see E. A. Nodiff et al., *J. Org. Chem.*, 25, 60 (1959)) and 4.7 g (0.0288 mole) of 3,4-dichlorophenol dissolved in 150 ml of DMSO was added 4.0 g (0.0288 mole) of $K_2CO_3$. The reaction mixture was heated at 125° C. for 3.5 hrs and the product recovered (6.15 g, 86.3% yield) as described in Example 18. Recrystallization from ethanol afforded purified 4-(4-((trifluoromethyl)sulfonyl)phenoxy)-1,2-dichlorobenzene, mp 77°–78° C.

EXAMPLE 26

N,N-Diethyl-4-(4-((trifluoromethyl)sulfonyl)phenoxy)-benzenesulfonamide

To a solution of 4.6 g (0.0188 mole) of 4-chlorophenyl trifluoromethyl sulfone and 4.8 g (0.0210 mole) of N,N-diethyl-4-hydroxybenzenesulfonamide in 80 ml of DMSO was added 2.9 g (0.0210 mole) of $K_2CO_3$. The mixture was heated at 100° C. for 3.25 hrs and cooled. The mixture was poured into aqueous NaOH and the crystalline product collected by filtration, washed well with water and dried, which gave 7.25 g (88.2% yield) of product. Recrystallization from 2-propanol afforded purified N,N-diethyl-4-(4-((trifluoromethyl)sulfonyl)-phenoxy)benzenesulfonamide, mp 83°–84° C.

EXAMPLE 27

1-(Methylthio)-4-(4-nitrophenoxy)benzene

A mixture of 23.6 g (0.150 mole) of 4-nitrochlorobenzene, 23.1 g (0.165 mole) of 4-(methylthio)phenol, 22.8 g (0.165 mole) of anhydrous $K_2CO_3$ and 150 ml of sulfolane was heated at 150° C. for 6 hrs. The product was recovered (39.1 g, 99.7% yield) as described in Example 1 and recrystallized from ethanol, which gave purified 1-(methylthio)-4-(4-nitrophenoxy)benzene, mp 59°–61° C.

EXAMPLE 28

1-(4-Methylthio)phenoxy)-2,4-dinitrobenzene

To a solution of 15.4 g (0.110 mole) of 4-(methylthio)-phenol dissolved in 150 ml of sulfolane was added 4.40 g (0.110 mole) of NaOH. The mixture was heated to 65° C. and 20.25 g (0.100 mole) of 2,4-dinitrochlorobenzene added and the reaction mixture heated at 65° C. for 3.25 hrs. The product was recovered (29.8 g, 97.4% yield) as described in Example 1 and recrystallized from ethanol, which gave purified 1-(4-(methylthio)phenoxy)-2,4-dinitrobenzene, mp 119°–120.5° C.

EXAMPLE 29

1-(Methylsulfinyl)-4-(4-nitrophenoxy)benzene

A solution of 10.0 g (0.0383 mole) of 1-(methylthio)-4-(4-nitrophenoxy)benzene and 7.76 g (0.0383 mole) of 85% 3-chloroperbenzoic acid dissolved in 500 ml of $CH_2Cl_2$ was stirred at ambient temperature for 3 days. The reaction mixture was extracted with aqueous $K_2CO_3$, water and dried ($Na_2SO_4$). Removal of solvent in vacuo afforded 10.3 g (97.2% yield) of product. Recrystallization from 2-propanol yielded purified 1-(methylsulfinyl)-4-(4-nitrophenoxy)benzene, mp 76°–78° C.

EXAMPLE 30

1-(4-(Methylsulfinyl)phenoxy)-2,4-dinitrobenzene, mp 126°–127° C.

The compound 1-(4-methylsulfinyl)phenoxy)-2,4-dinitrobenzene was prepared (97.1% yield) utilizing essentially the same procedure described in Example 29 and purified by recrystallization from ethanol.

EXAMPLE 31

1-(4-(Methylsulfonyl)phenoxy)-2,4-dinitrobenzene

To a solution of 10.0 g (0.0327 mole) of 1-(4-(methylthio)phenoxy)-2,4-dinitrobenzene dissolved in 75 ml of glacial acetic acid was added dropwise 14.85 g of 30% aqueous hydrogen peroxide (0.131 mole) at 75° C. The reaction mixture was heated at 75° C. for 4 hrs, and 10.6 g (96.4% yield) of the product recovered as described in Example 1. Recrystallization from ethanol afforded purified 1-(4-(methylsulfonyl)phenoxy)-2,4-dinitrobenzene, mp 176°–177° C.

EXAMPLE 32

1-(Methylsulfonyl)-4-(4-nitrophenoxy)benzene, mp 132.5°–133.5° C.

The compound 1-(methylsulfonyl)-4-(4-nitrophenoxy)benzene was prepared (94.6% yield) utilizing essentially the same procedure set forth in Example 31.

The physical properties of the above examples are summarized in Table 1.

TABLE 1

| Compound Example No. | R | m | $R_1^x$ | $R_2^x$ | $R_3^x$ | Mp, °C. | Calculated % C | % H | % N | Found % C | % H | % N |
|---|---|---|---|---|---|---|---|---|---|---|---|---|
| 1 | CH$_3$ | 2 | H | 4-Cl | 3-Cl | 124.5–125.5 | 49.22 | 3.18 | — | 49.2 | 3.22 | — |
| 2 | CH$_3$ | 2 | H | 4-Cl | H | 111–112 | 55.22 | 3.92 | — | 55.1 | 3.92 | — |
| 3 | CH$_3$ | 2 | H | 4-CCH$_3$ ‖ O | H | 131–132.5 | 62.05 | 4.86 | — | 61.85 | 4.81 | — |
| 4 | CH$_3$ | 2 | H | 4-C(=O)—C$_6$H$_5$ | H | 164–165 | 68.16 | 4.58 | — | 68.0 | 4.65 | — |
| 5 | CH$_3$ | 0 | H | 4-CN | H | 65–66 | 69.68 | 4.60 | 5.81 | 70.0 | 4.72 | 5.90 |
| 6 | CH$_3$ | 1 | H | 4-Cl | 3-Cl | 92–93.5 | 51.84 | 3.35 | — | 51.9 | 3.48 | — |
| 7 | CH$_3$ | 1 | H | 4-CN | H | Oil | 65.35 | 4.31 | 5.44 | 64.2 | 4.44 | 5.37 |
| 8 | CH$_3$ | 2 | H | 4-CN | H | 127–128.5 | 61.52 | 4.06 | 5.13 | 61.4 | 4.14 | 5.10 |
| 9 | CH$_3$ | 2 | H | 4-Sr | H | 127.5–129 | 47.72 | 3.39 | — | 47.9 | 3.44 | — |
| 10 | C$_6$H$_5$ | 2 | H | 4-Cl | 3-Cl | 145–146 | 57.00 | 3.19 | — | 56.99 | 3.32 | — |
| 11 | C$_6$H$_5$ | 2 | H | 4-SO$_2$N(CH$_3$)$_2$ | H | 99–100 | 57.53 | 4.59 | 3.36 | 57.44 | 4.68 | 3.40 |
| 12 | CH$_3$ | 2 | H | 4-SO$_2$N(CH$_3$)$_2$ | H | 127.5–130 | 50.69 | 4.82 | 3.94 | 50.65 | 4.86 | 3.89 |
| 13 | CH$_3$ | 2 | H | 4-SO$_2$N(C$_2$H$_5$)$_2$ | H | 101–103.5 | 53.24 | 5.52 | 3.65 | 53.19 | 5.50 | 3.62 |
| 14 | CH$_3$ | 2 | 2'-Cl | 4-Cl | 3-Cl | 102–104 | 44.40 | 2.58 | — | 44.4 | 2.61 | — |
| 15 | CH$_3$ | 2 | 2'-NO$_2$ | 4-Cl | 3-Cl | 173–174 | 43.11 | 2.50 | 3.87 | 43.07 | 2.61 | 3.91 |
| 16 | CH$_3$ | 2 | 2'-NH$_2$ | 4-Cl | 3-Cl | 119–121 | 47.00 | 3.34 | 4.22 | 46.94 | 3.46 | 4.33 |
| 17 | CH$_3$ | 2 | 2'-CN | 4-Cl | 3-Cl | 162–163 | 49.14 | 2.65 | 4.09 | 49.05 | 2.76 | 4.19 |
| 18 | CH$_3$ | 2 | H | 4-OCH$_3$ | H | 151.5–153 | 60.41 | 5.07 | — | 60.3 | 5.09 | — |
| 19 | CH$_3$ | 2 | 3'-CH$_3$ | 4-Cl | 3-Cl | 154–156 | 50.76 | 3.65 | — | 50.8 | 3.67 | — |
| 20 | CH$_3$ | 2 | H | 4-CH$_2$—C$_6$H$_5$ | H | 109–110 | 70.98 | 5.36 | — | 70.9 | 5.43 | — |
| 21 | CH$_3$ | 2 | H | 4-OH | H | 129–130 | 59.07 | 4.58 | — | 59.1 | 4.63 | — |
| 22 | CH$_3$ | 2 | H | 4-OCF$_2$CHCl$_2$ | H | 67–70 | 45.35 | 3.05 | — | 45.04 | 2.92 | — |
| 23 | CH$_3$ | 2 | H | 4-OCH$_2$CN | H | 114–115.5 | 59.39 | 4.32 | 4.62 | 59.5 | 4.51 | 4.56 |
| 24 | CH$_3$ | 2 | H | 4-OCH$_2$CH$_2$N(C$_2$H$_5$)$_2$ | H | 92.5–94 | 62.78 | 6.93 | 3.85 | 62.80 | 6.88 | 3.85 |
| 25 | CF$_3$ | 2 | H | 4-Cl | 3-Cl | 77–78 | 42.06 | 1.90 | — | 42.0 | 1.92 | — |
| 26 | CF$_3$ | 2 | H | 4-SO$_2$N(C$_2$H$_5$)$_2$ | H | 83–84 | 46.67 | 4.15 | 3.20 | 46.8 | 4.18 | 3.12 |
| 27 | CH$_3$ | 0 | H | 4-NO$_2$ | H | 59–61 | 59.75 | 4.24 | 5.36 | 59.7 | 4.32 | 5.23 |
| 28 | CH$_3$ | 0 | H | 4-NO$_2$ | 2-NO$_2$ | 119–120.5 | 50.97 | 3.29 | 9.15 | 51.0 | 3.32 | 9.32 |
| 29 | CH$_3$ | 1 | H | 4-NO$_2$ | H | 76–78 | 56.31 | 4.00 | 5.05 | 56.2 | 4.09 | 5.01 |
| 30 | CH$_3$ | 1 | H | 4-NO$_2$ | 2-NO$_2$ | 126–127 | 48.44 | 3.13 | 8.69 | 48.7 | 3.26 | 8.64 |
| 31 | CH$_3$ | 2 | H | 4-NO$_2$ | 2-NO$_2$ | 176–177 | 46.15 | 2.98 | 8.28 | 46.2 | 3.10 | 8.06 |
| 32 | CH$_3$ | 2 | H | 4-NO$_2$ | H | 132.5–133.5 | 53.23 | 3.78 | 4.78 | 53.4 | 3.82 | 4.71 |

$^x$The numbers accompanying the various substituents presented in the $R_1$, $R_2$, and $R_3$ columns designate the ring position of the indicated substituent as determined according to the following formula:

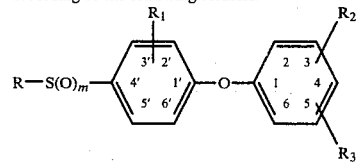

The compounds of the invention have antiviral activity, and have been found to be particularly effective against picornaviruses, i.e., the small ribonucleic acid viruses. The picornaviruses include viruses such as Coxsackieviruses, Rhinoviruses and a number of plant disease viruses. There is some compound-to-compound variation in antiviral potency and spectrum of antiviral activity, and in toxicity and side effects, as illustrated below.

Antiviral activity for the subject compounds was demonstrated utilizing the following tissue culture testing procedure:

Monolayered HeLa cells in 16 millimeter (mm) tissue culture dishes were treated with 1 ml of culture medium (Eagles medium supplemented with fetal calf serum) containing subject compound at an appropriate concentration or containing no compound at all. Culture media such as those described herein are more fully described in standard texts, as for example, Kuchler's Biochemical Methods in Cell Culture and Virology, Dowden, Hutchinson and Ross, Inc., Stroudsberg, Pa. (1977). Following treatment, cells were challenged with 0.05 ml of rhinovirus type 1A (RV-1A), rhinovirus type 2 (RV-2) or Coxsackie A$_{21}$ virus (Cox A$_{21}$) in culture medium. Some of the compounds were also tested against rhinovirus type 5 (RV-5), rhinovirus type 8 (RV-8) or rhinovirus type 64 (RV-64). Cell controls received no viruses. Cultures were observed for compound cytotoxicity and viral cytopathic effect (CPE) at 48 and 72 hours post-treatment.

In addition, some of the compounds were tested in animals utilizing the following procedure, hereinafter referred to as the "Single Oral Dose" test. Swiss male mice, 10–12 grams in weight were challenged intraperitoneally (IP) with 0.2 ml of a normally lethal dose, i.e. a virus dose sufficient to cause ≅80–100% mortality in infected animals within 10 days of challenge of Cox $A_{21}$, in phosphate buffered saline containing 1% heat inactivated fetal calf serum. Three hours later mice were treated orally (P.O.) with 0.2 ml of compound suspended in 0.5% hydroxypropyl methylcellulose (Methocel) or with 0.2 ml of 0.5% Methocel containing no compound. Compound solutions had a concentration of 5 milligrams/milliliter (mg/ml), 10 mg/ml, 20 mg/ml or 30 mg/ml, thus 0.2 ml of compound suspended in 0.5 percent Methocel represents a dosage of 100 milligrams/kilogram (mg/kg), 200 mg/kg, 400 mg/kg or 600 mg/kg, respectively. Mice were observed daily for 7–10 days post-challenge and deaths recorded. A modified Mantel-Haenzel combined chi-square procedure was used to determine significant difference between virus control and treated groups. Chi-square values greater than 3.84 are considered significant (95% confidence level) in this test.

Some of the compounds were also tested in animals utilizing the following procedure, hereinafter referred to as the "Continuous Oral Feeding" test. Coxsackie $A_{21}$ virus grown on HeLa cells was administered at a concentration that produces 80 to 100% deaths in mice weighing 10 to 11 grams within 10 days, when the mice are injected (IP) with 0.2 ml of virus preparation. Mice were placed on diets containing test compound dispersed in plain commercially available rodent mash chow at a concentration of 0.06% (weight percent) on day 0. On day 1 the mice were challenged with the virus preparation, 0.2 ml/mouse, (IP). Deaths in both control and experimental groups were recorded for the 10 days and the results analyzed by a chi-square ($\chi^2$) test. Chi-square values greater than 3.84 indicate the compound is active (95% confidence level).

The results obtained from the testing described above are summarized in Table 2.

TABLE 2

| Compound Example Number | Cytotoxicity* (μg/ml) | Tissue Culture Testing** (μg/ml) | | | | | | Animal Testing | | | |
|---|---|---|---|---|---|---|---|---|---|---|---|
| | | | | | | | | Single Oral Dose | | Continuous Oral Feeding | |
| | | RV-1A | RV-2 | Cox $A_{21}$ | RV-5 | RV-8 | RV-64 | Dose (mg/kg) | $X^2$ | Dose*** | $X^2$ |
| 1 | 50–100 (G.I.) | 0.25 | 0.25 | 2.5 | NA | ±50 | 0.25 | 400 | 38.16 | 0.06% | 23.49 |
| 2 | 10 (G.I.) | 1.25 | 1.25 | 0.625 | | | | 100 | 47.76 | 0.06% | 9.20 |
| 3 | 50 | 25 | 12.5 | <6.25 | 25 | 25 | <6.25 | 600 | 9.153 | 0.06% | 4.90 |
| 4 | >100 | NA | 50 | <<6.25 | NA | NA | 100 | | | 0.06% | 27.1 |
| 5 | 6.25 | <3.125 | <3.125 | <<3.125 | | NA | | 600 | 7.218 | 0.06% | 2.315 |
| 6 | 12.5 | <0.31 | <0.31 | NA | NA | NA | <0.31 | 100 | 33.23 | 0.06% | 13.6 |
| 7 | 25 | 3.125 | 3.125 | 3.125 | | NA | | 600 | 5.699 | | |
| 8 | 50 | 12.5 | 12.5 | <<6.25 | 12.5 | 25 | 12.5 | 600 | 4.23 | 0.06% | 7.7 |
| 9 | 12.5 | <<3.125 | <<3.125 | <<3.125 | 12.5 | 12.5 | | | | 0.06% | 27.794 |
| 10 | 50 | NA | 6.25 | 6.25 | | | | 600 | 2.689 | 0.06% | 5.921 |
| 11 | 1.25 | 0.625 | 0.625 | 0.625 | | | | 600 | 1.73 | 0.06% | 3.59 |
| 12 | 100 (G.I.) | NA | NA | 50 | | | | | | 0.06% | 3.126 |
| 13 | 100 (G.I.) | 50 | NA | 25 | | | | | | 0.06% | 1.174 |
| 14 | 50 | 12.5 | ≦6.25 | 12.5 | | | | 600 | 9.11 | 0.06% | 10.9 |
| 15 | >100 | NA | 6.25 | NA | | | | | | 0.06% | 0.303 |
| 16 | ≦6.25 | <6.25 | 6.25 | 6.25 | | | | 600 | 9.47 | 0.06% | 2.23 |
| 17 | >100 | 12.5 | 25 | 12.5 | | | | | | 0.06% | 0.762 |
| 18 | >50 | 6.25 | 12.5 | 25 | NA | NA | 12.5 | | | | |
| 19 | >50 | <3.125 | 6.25 | NA | 12.5 | NA | <3.125 | | | | |
| 20 | 5 | 2.5 | 1.25 | 2.5 | 5 | 5 | 2.5 | | | | |
| 21 | 25 | ±25 | ±25 | NA | NA | NA | NA | | | | |
| 22 | 2.5 | 2.5 | 1.25 | 0.625 | ±1.25 | NA | NA | | | | |
| 23 | 10 | 2.5 | 5 | 2.5 | 5 | 5 | 10 | | | | |
| 24 | ≦20 | 1.25 | NA | NA | 2.5 | NA | NA | | | | |
| 25 | >50 | 12.5 | 6.25 | <3.125 | NA | NA | NA | | | | |
| 26 | 0.625 | 0.3125 | 0.3 | ≦0.3 | 0.625 | ≦0.3125 | 0.625 | | | | |
| 27 | 12.5 | 6.25 | ≦6.25 | <6.25 | | | | 600 | 47.01 | 0.06% | 31.02 |
| 28 | 50–100 (G.I.) | ≦6.25 | <6.25 | ≦6.25 | | | | 600 | 6.758 | 0.06% | 1.472 |
| 29 | 25 | ≦6.25 | ≦6.25 | <6.25 | | | | 200 | 33.43 | 0.06% | 31.02 |
| 30 | 12.5 | NA | ±6.25 | 6.25 | | | | 600 | 12.159 | 0.06% | 1.136 |
| 31 | 25 | ±12.5 | ±12.5 | ≦6.25 | | | | 600 | 2.26 | 0.06% | 0.252 |
| 32 | 50 | 12.5 | ≦6.25 | <6.25 | | | | 600 | 50.28 | 0.06% | 31.02 |

*Cytotoxicity figures represent the concentration of the compound, micrograms/milliliter (μg/ml) found to be toxic to the cell.
**Lowest concentration of the compound (μg/ml) necessary to cause a 50 percent reduction in cytopathic effect.
***Percent (by weight) of test compound in the diet fed to test animals.
The symbol "NA" indicates that the compound was not active against that particular virus at the standard test conditions; "<" means "less than"; ">" means "greater than"; "≦" means "less than or equal to"; "±" means "approximately"; "<<" means "considerably less than" and "G.I." means "growth inhibition" and indicates that at the concentration shown, the compound inhibited the growth of the tissue culture.

The data in Table 2 demonstrate the antiviral activity of representative compounds falling within the scope of the present invention.

The tissue culture test data indicate that all of the test compounds are active against at least one of the three test viruses, (RV-1A, RV-2 or Cox $A_{21}$). In addition, several of the test compounds have exhibited antiviral activity with respect to test viruses RV-5, RV-8 or RV-64.

Furthermore, some of the compounds have demonstrated (at the 95% confidence level, i.e., have a $X^2$ value greater than 3.84) that they are active antiviral compounds in testing with mice.

Of particular interest is the compound of Example 1, i.e., 4-(4-(methylsulfonyl)phenoxy)-1,2-dichlorobenzene, which exhibited antiviral activity in both the "Single Oral Dose" and "Continuous Oral Feeding" tests. A compound which can be administered orally and still retain antiviral activity has distinct advantages since it can readily incorporated in the diets of mammals, as exemplified in the "Continuous Oral Feeding" test, or administered to mammals orally in various compositions comprising the active compound and a pharmaceutically-acceptable carrier. The compound 4-(4-(methylsulfonyl)phenoxy)-1,2-dichlorobenzene has exhibited antiviral activity against a broad spectrum of viruses in other tissue culture testing as follows:

Solutions of 4-(4-(methylsulfonyl)phenoxy)-1,2-dichlorobenzene were prepared by dissolving 5 milligrams of the compound in 0.1 ml dimethyl sulfoxide and incubating at 56° C. for at least 15 minutes. This solution was added to 0.9 ml of warmed (56° C.) maintenance medium (49% Eagles, 49% medium 199, 2% fetal calf serum and antibiotics), and the resulting 1.0 ml was then added to 9 ml of warmed (56° C.) maintenance medium. From this solution the final concentrations of 100, 50, 25, or 12.5 μg/ml were made up with maintenance medium.

Triplicate cell culture tubes (Wl-38 human embryonic lung cell culture tubes) were fed with 1 ml of medium containing the compound at specified concentrations and inoculated with 3–300 TCID$_{50}$ (3–300 times the tissue culture infective dose 50, i.e., the dose required to infect 50% of the cell cultures tested. Simultaneous viral titrations were performed. The tissue cultures were supplemented with fresh medium when necessary (around 3–4 days) until viral titrations were completed.

The cell culture tubes were examined daily for cytopathic effect. Tests were judged complete when virus control titration tubes showed 75% or greater destruction of cell sheets. Comparisons were made at that time with the percentage of cell sheet destruction in tubes containing virus compound mixtures. Observed differences of 75% or more were graded "+", 74–50% as "±", and less than 50% as "−" inhibition.

In the above-noted tests, the compound 4-(4-(methylsulfonyl)phenoxy)-1,2-dichlorobenzene at a concentration of 25 micrograms per milliliter (μg/ml) inhibited the multiplication of most of the 20 different rhinoviruses against which it was tested, i.e., was graded as "+" against 17 different rhinoviruses utilized for testing, which viruses were as follows: an untyped rhinovirus designated as "Hank's (untyped)" and these additional rhinovirus types: type 4, type 6, type 10, type 13, type 17, type 19, type 21, type 29, type 39, type 56, type 58, type 59, type 60, type 64, type 74 and type 81; was graded as "±" against rhinovirus type 68 and was graded as "−" against rhinovirus type 8 and rhinovirus type 75.

The results of the above-noted testing indicate that the compound 4-(4-(methylsulfonyl)phenoxy)-1,2-dichlorobenzene is particularly effective against Picornaviruses, i.e. small ribonucleic acid (rna) viruses, as for example, the Coxsackieviruses and Rhinoviruses. They further indicate that such compound has a broad spectrum of activity against Picornaviruses.

A distinct advantage of the compound is its low toxicity, in testing in rats it was found that the compound had an acute oral toxicity of greater than 2 grams/kilogram (kg) and with intraperitoneal administration greater than 1 gram/kg. Testing in beagle dogs indicated an acute oral toxicity of greater than 2 grams/kg.

Because of its many distinct advantages (broad spectrum antiviral activity at low compound concentration, low toxicity, antiviral activity when administered to animals orally, etc.), the compound 4-(4-(methylsulfonyl)phenoxy)-1,2-dichlorobenzene is the preferred embodiment of the present invention.

In using the subject compounds, a virus or virus host cell is contacted with an amount of one or more of the compounds effective to inhibit the virus. Although the invention should not be construed as limited to any particular theory of action, it appears that the compounds act to inhibit virus in host cells, rather than by direct chemical or physical inactivation of the virus particle apart from the cell. In antiviral applications carried out in non-living environments, contacting should be carried out in a manner which ensures continued presence of an effective amount of the compound when subsequent contact with host cells occurs. Preferably, the compounds are used by contacting the host cells with an effective antiviral amount (i.e., the amount which must be employed to achieve significant viral inhibition) of one or more of the compounds. The contacting can be carried out directly, as by addition of the compound to cells in tissue culture, to inhibit contaminating picornaviruses. Contacting can also be carried out by administering an antiviral dosage of a compound of the invention to an animal (preferably, a mammal). The compounds can be administered to animals parenterally (for example, by intraperitoneal, subcutaneous or intravenous injection) or orally, and the oral antiviral activity of certain of the compounds is a feature of the invention. In such applications, an effective antiviral dose of one or more of the compounds is administered to an animal. Selection of the compound or compounds for administration to animals in particular cases is dictated by considerations such as toxicity, mutagenicity, ease of administration, antiviral activity (potency), stability, compatibility with suitable carriers, etc.

The exact amount of the compound or compounds to be employed, i.e., the amount of the subject compound or compounds sufficient to provide the desired effect, depends on various factors such as the compound employed; type of contacting or administration; the size, age and species of animal; the route, time and frequency of administration; the virus or viruses involved, and whether or not the compound is administered prophylactically or is administered to an infected animal to inhibit the infecting virus. In particular cases, the amount to be administered can be ascertained by conventional range finding techniques, for example, by observing the effect produced at different rates using conventional virus assay procedures.

The compounds are preferably administered in the form of a composition comprising the compound in admixture with a pharmaceutically-acceptable carrier, i.e., a carrier which is chemically inert to the active compound and which has no detrimental side effects or toxicity under the conditions of use. As shown above, the compounds when administered to tissue culture medium exhibit significant antiviral activity at low concentrations, such as, for example, the 0.25 μg/ml of 4-(4-(methylsulfonyl)phenoxy)-1,2-dichlorobenzene which caused a 50% reduction in cytopathic effect in testing against test viruses RV-1A, RV-2 and RV-64.

Such compositions can contain from about 0.1 microgram or less of the active compound per milliliter of carrier to about 99 percent by weight of the active compound in combination with a pharmaceutically-acceptable carrier.

Preferred compositions include compositions containing from about 0.1 μg of active compound per milliliter of carrier to about 0.0025 to about 0.05 to about 0.25 to about 0.5 to about one to about 10 to about 25 to about 50 percent by weight of active compound in a pharmaceutically-acceptable carrier.

The compositions can be in solid forms such as tablets, capsules, granulations, feed mixes, feed supplements and concentrates, powders, granules, or the like; as well as liquid forms such as sterile injectable suspensions, orally administered suspensions, or solutions. The pharmaceutically-acceptable carriers can include excipients such as surface active dispersing agents, suspending agents, tableting binders, lubricants, flavors and colorants. Suitable excipients are disclosed, for example, in texts such as Remington's Pharmaceutical Manufacturing, Thirteenth Edition, Mack Publishing Co., Easton Pa. (1965). What is claimed is:

1. A compound corresponding to the formula:

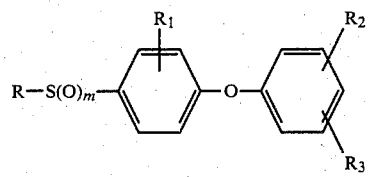

wherein m represents the integer 0, 1 or 2; R represents, $(C_1-C_3)$ alkyl or phenyl; $R_1$ represents hydrogen, bromo, chloro, fluoro, nitro, amino, $(C_1-C_3)$ alkyl, $(C_1-C_3)$ alkoxy or trifluoromethyl; $R_2$ represents hydroxyl, bromo, chloro, fluoro, acetyl, benzoyl, a benzoyl radical in which the benzene ring is substituted with one to five substituents selected from bromo, chloro, fluoro, methyl or methoxy, $(C_1-C_3)$ alkyl, $(C_1-C_3)$ alkoxy, an alkoxy group substituted with one or more substituents selected from bromo, chloro or fluoro, benzyl, a benzyl radical in which the benzene ring is substituted with one to five substituents selected from bromo, chloro, fluoro, methyl or methoxy, $(C_1-C_3)$ alkylthio, $(C_1-C_3)$ alkylsulfinyl, $(C_1-C_3)$ alkylsulfonyl, or the radical $-O(CH_2)_nR_4$ wherein n represents the integer 1, 2 or 3; and $R_4$ represents di$(C_1-C_3)$alkylamino; $R_3$ represents hydrogen, hydroxyl, bromo, chloro, fluoro, acetyl, benzoyl, a benzoyl radical in which the benzene ring is substituted with one to five substituents selected from bromo, chloro, fluoro, methyl or methoxy, $(C_1-C_3)$ alkyl, $(C_1-C_3)$ alkoxy, an alkoxy group substituted with one or more substituents selected from bromo, chloro or fluoro, benzyl, a benzyl radical in which the benzene ring is substituted with one to five substituents selected from bromo, chloro, fluoro, methyl or methoxy, $(C_1-C_3)$ alkylthio, $(C_1-C_3)$ alkylsulfinyl, $(C_1-C_3)$ alkylsulfonyl, or the radical $-O(CH_2)_nR_4$ wherein n represents the integer 1, 2 or 3; and $R_4$ represents di$(C_1-C_3)$alkylamino; provided that when $R_2$ is bromo, chloro, fluoro, $(C_1-C_3)$ alkyl, $(C_1-C_3)$ alkoxy, $(C_1-C_3)$ alkylthio, $(C_1-C_3)$ alkylsulfinyl or $(C_1-C_3)$ alkylsulfonyl and $R_3$ is hydrogen, bromo, chloro, fluoro, $(C_1-C_3)$ alkyl, $(C_1-C_3)$ alkoxy, $(C_1-C_3)$ alkylthio, $(C_1-C_3)$ alkylsulfinyl or $(C_1-C_3)$ alkylsulfonyl then $R_1$ is amino.

2. A compound corresponding to the formula:

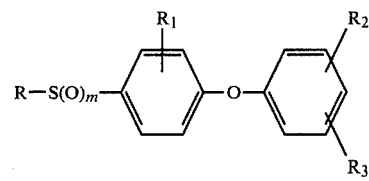

wherein m represents the integer 0, 1 or 2; R represents trihalomethyl; $R_1$ represents hydrogen, bromo, chloro, fluoro, nitro, amino, $(C_1-C_3)$ alkyl, $(C_1-C_3)$ alkoxy or trifluoromethyl; $R_2$ represents hydroxyl, bromo, chloro, fluoro, acetyl, benzoyl, a benzoyl radical in which the benzene ring is substituted with one to five substituents selected from bromo, chloro, fluoro, methyl or methoxy, $(C_1-C_3)$ alkyl, $(C_1-C_3)$ alkoxy, an alkoxy group substituted with one or more substituents selected from bromo, chloro or fluoro, benzyl, a benzyl radical in which the benzene ring is substituted with one to five substituents selected from bromo, chloro, fluoro, methyl or methoxy, $(C_1-C_3)$ alkylthio, $(C_1-C_3)$ alkylsulfinyl, $(C_1-C_3)$ alkylsulfonyl, or the radical $-O(CH_2)_nR_4$ wherein n represents the integer 1, 2 or 3; and $R_4$ represents di$(C_1-C_3)$alkylamino; $R_3$ represents hydrogen, hydroxyl, bromo, chloro, fluoro, acetyl, benzoyl, a benzoyl radical in which the benzene ring is substituted with one to five substituents selected from bromo, chloro, fluoro, methyl or methoxy, $(C_1-C_3)$ alkyl, $(C_1-C_3)$ alkoxy, an alkoxy group substituted with one or more substituents selected from bromo, chloro or fluoro, benzyl, a benzyl radical in which the benzene ring is substituted with one to five substituents selected from bromo, chloro, fluoro, methyl or methoxy, $(C_1-C_3)$ alkylthio, $(C_1-C_3)$ alkylsulfinyl, $(C_1-C_3)$ alkylsulfonyl, or the radical $-O(CH_2)_nR_4$ wherein n represents the integer 1, 2 or 3; and $R_4$ represents di$(C_1-C_3)$alkylamino.

3. The compound of claim 1 wherein m represents the integer 0, 1 or 2; R represents trifluoromethyl; $R_1$ represents hydrogen; $R_2$ represents bromo or chloro; and $R_3$ represents hydrogen, bromo or chloro.

4. The compound of claim 1 which is 1-(4-(4-(methylsulfonyl)phenoxy)phenyl)ethanone.

5. The compound of claim 1 which is (4-(4-(methylsulfonyl)phenoxy)phenyl)phenylmethanone.

6. The compound of claim 1 which is 2-(3,4-dichlorophenoxy)-5-(methylsulfonyl)benzenamine.

7. The compound of claim 1 which is 4-(4-(methylsulfonyl)phenoxy)-1-methoxybenzene.

8. The compound of claim 1 which is 1-(4-(methylsulfonyl)phenoxy)-4-(phenylmethyl)benzene.

9. The compound of claim 1 which is 4-(4-(methylsulfonyl)phenoxy)phenol.

10. The compound of claim 1 which is 1-(2,2-dichloro-1,1-difluoroethoxy)-4-(4-(methylsulfonyl)phenoxy)benzene.

11. The compound of claim 1 which is N,N-diethyl-2-(4-(4-(methylsulfonyl)phenoxy)phenoxy)ethylamine.

12. The compound of claim 2 which is 4-(4-((trifluoromethyl)sulfonyl)phenoxy)-1,2-dichlorobenzene.

13. A method for inhibiting viruses which comprises contacting viruses or virus host cells with an effective virus inhibiting amount of a compound corresponding to the formula:

$$R-S(O)_m-\underset{\underset{R_1}{|}}{\text{C}_6\text{H}_4}-O-\underset{\underset{R_6}{|}}{\text{C}_6\text{H}_3}-R_5$$

wherein m represents the integer 0, 1 or 2; R represents trihalomethyl, (C$_1$-C$_3$) alkyl or phenyl; R$_1$ represents hydrogen, bromo, chloro, fluoro, nitro, amino, (C$_1$-C$_3$) alkyl, (C$_1$-C$_3$) alkoxy or trifluoromethyl; and R$_5$ and R$_6$ each independently represent hydrogen, nitro, hydroxyl, bromo, chloro, fluoro, acetyl, benzoyl, a benzoyl radical in which the benzene ring is substituted with one to five substitutents selected from bromo, chloro, fluoro, methyl or methoxy, (C$_1$-C$_3$) alkyl, (C$_1$-C$_3$) alkoxy, an alkoxy group substituted with one or more substituents selected from bromo, chloro or fluoro, benzyl, a benzyl radical in which the benzene ring is substituted with one to five substituents selected from bromo, chloro, fluoro, methyl or methoxy, (C$_1$-C$_3$) alkylthio, (C$_1$-C$_3$) alkylsulfinyl, (C$_1$-C$_3$) alkylsulfonyl, or the radical —O(CH$_2$)$_n$R$_4$ wherein n represents the integer 1, 2, or 3; and R$_4$ represents di(C$_1$-C$_3$)alkylamino.

14. The method of claim 13 wherein the compound is contacted with a virus host cell.

15. The method of claim 13 wherein the compound is contacted with virus and mammalian cells.

16. The method of claim 13 wherein the viruses are picornaviruses.

17. The method of claim 13 wherein m represents the integer 0, 1 or 2; R represents trifluoromethyl, methyl or phenyl; R$_1$ represents hydrogen; R$_5$ represents bromo or chloro; and R$_6$ represents hydrogen, bromo or chloro.

18. The method of claim 17 wherein m represents the integer 0, 1 or 2; R represents methyl; R$_1$ represents hydrogen; R$_5$ represents bromo or chloro; and R$_6$ represents hydrogen, bromo or chloro.

19. The method of claim 18 wherein the compound is 4-(4-(methylsulfonyl)phenoxy)-1,2-dichlorobenzene.

20. The method of claim 18 wherein the compound is 4-(4-(methylsulfonyl)phenoxy)-1-chlorobenzene.

21. The method of claim 18 wherein the compound is 1-bromo-4-(4-(methylsulfonyl)phenoxy)benzene.

22. A method for inhibiting viruses which comprises administering to an animal an effective virus inhibiting amount of a compound corresponding to the formula:

$$R-S(O)_m-\underset{\underset{R_1}{|}}{\text{C}_6\text{H}_4}-O-\underset{\underset{R_6}{|}}{\text{C}_6\text{H}_3}-R_5$$

wherein m represents the integer 0, 1 or 2; R represents trihalomethyl, (C$_1$-C$_3$) alkyl or phenyl; R$_1$ represents hydrogen, bromo, chloro, fluoro, nitro, amino, (C$_1$-C$_3$) alkyl, (C$_1$-C$_3$) alkoxy or trifluoromethyl; and R$_5$ and R$_6$ each independently represent hydrogen, nitro, hydroxyl, bromo, chloro, fluoro, acetyl, benzoyl, a benzoyl radical in which the benzene ring is substituted with one to five substitutents selected from bromo, chloro, fluoro, methyl or methoxy, (C$_1$-C$_3$) alkyl, (C$_1$-C$_3$) alkoxy, an alkoxy group substituted with one or more substituents selected from bromo, chloro or fluoro, benzyl, a benzyl radical in which the benzene ring is substituted with one to five substituents selected from bromo, chloro, fluoro, methyl or methoxy, (C$_1$-C$_3$) alkylthio, (C$_1$-C$_3$) alkylsulfinyl, (C$_1$-C$_3$) alkylsulfonyl, or the radical —O(CH$_2$)$_n$R$_4$ wherein n represents the integer 1, 2, or 3; and R$_4$ represents di(C$_1$-C$_3$)alkylamino.

23. The method of claim 22 wherein the animal is a mammal.

24. The method of claim 22 wherein the animal is an animal infected with picornavirus.

25. The method of claim 24 wherein the picornavirus is a Rhinovirus.

26. The method of claim 24 wherein the picornavirus is a Coxsackievirus.

27. The method of claim 22 wherein m represents the integer 0, 1 or 2; R represents trifluoromethyl, methyl or phenyl; R$_1$ represents hydrogen; R$_5$ represents bromo or chloro; and R$_6$ represents hydrogen, bromo or chloro.

28. The method of claim 27 wherein m represents the integer 0, 1 or 2; R represents methyl; R$_1$ represents hydrogen; R$_5$ represents bromo or chloro; and R$_6$ represents hydrogen, bromo or chloro.

29. The method of claim 28 wherein the compound is 4-(4-(methylsulfonyl)phenoxy)-1,2-dichlorobenzene.

30. The method of claim 28 wherein the compound is 4-(4-(methylsulfonyl)phenoxy)-1-chlorobenzene.

31. The method of claim 28 wherein the compound is 1-bromo-4-(4-(methylsulfonyl)phenoxy)benzene.

32. A composition for inhibiting viruses comprising an inert carrier in combination with an effective virus inhibiting amount of a compound corresponding to the formula:

$$R-S(O)_m-\underset{\underset{R_1}{|}}{\text{C}_6\text{H}_4}-O-\underset{\underset{R_6}{|}}{\text{C}_6\text{H}_3}-R_5$$

wherein m represents the integer 0, 1 or 2; R represents trihalomethyl, (C$_1$-C$_3$) alkyl or phenyl; R$_1$ represents hydrogen, bromo, chloro, fluoro, nitro, amino, (C$_1$-C$_3$) alkyl, (C$_1$-C$_3$) alkoxy or trifluoromethyl; and R$_5$ and R$_6$ each independently represent hydrogen, nitro, hydroxyl, bromo, chloro, fluoro, acetyl, benzoyl, a benzoyl radical in which the benzene ring is substituted with one to five substituents selected from bromo, chloro, fluoro, methyl or methoxy, (C$_1$-C$_3$) alkyl, (C$_1$-C$_3$) alkoxy, an alkoxy group substituted with one or more substituents selected from bromo, chloro or fluoro, benzyl, a benzyl radical in which the benzene ring is substituted with one to five substituents selected from bromo, chloro, fluoro, methyl or methoxy, (C$_1$-C$_3$) alkylthio, (C$_1$-C$_3$) alkylsulfinyl, (C$_1$-C$_3$) alkylsulfonyl, or the radical —O(CH$_2$)$_n$R$_4$ wherein n represents the integer 1, 2 or 3; and R$_4$ represents di(C$_1$-C$_3$)alkylamino.

33. The composition of claim 32 wherein the inert carrier is a non-toxic carrier.

34. The composition of claim 33 wherein the non-toxic carrier is a pharmaceutically-acceptable carrier.

35. The composition of claim 34 wherein m represents the integer 0, 1 or 2; R represents trifluoromethyl, methyl or phenyl; $R_1$ represents hydrogen; $R_5$ represents bromo or chloro; and $R_6$ represents hydrogen, bromo or chloro.

36. The composition of claim 35 wherein m represents the integer 0, 1 or 2; R represents methyl; $R_1$ represents hydrogen, $R_5$ represents bromo or chloro; and $R_6$ represents hydrogen, bromo or chloro.

37. The composition of claim 36 wherein the compound is 4-(4-(methylsulfonyl)phenoxy)-1,2-dichlorobenzene.

38. The composition of claim 36 wherein the compound is 4-(4-(methylsulfonyl)phenoxy)-1-chlorobenzene.

39. The composition of claim 36 wherein the compound is 1-bromo-4-(4-(methylsulfonyl)phenoxy)benzene.

* * * * *

UNITED STATES PATENT AND TRADEMARK OFFICE
CERTIFICATE OF CORRECTION

PATENT NO. : 4,349,568

DATED : September 14, 1982

INVENTOR(S) : Lowell D. Markley, et al.

It is certified that error appears in the above—identified patent and that said Letters Patent is hereby corrected as shown below:

Column 6, line 42, "phenoxy]benzene," should read --phenoxy)benzene,--.

Column 6, line 68, "benzenmine" should read --benzenamine--.

Column 7, line 32, "contrued" should read --construed--.

Column 9, line 49, "4-(4-methylsulfonyl)" should read -- 4-(4-(methylsulfonyl)--.

Column 9, line 59, "4-(4-methylsul-" should read -- 4-(4-(methylsul- --.

Column 10, line 57, "4-(4-methylsulfonyl)" should read -- 4-(4-(methylsulfonyl)--.

Column 12, line 24, "1-(4-Methylsulfonyl)" should read -- 1-(4-(Methylsulfonyl) --.

Column 12, line 65, "rmoved" should read --removed--.

Column 13, line 5, "4-(4-Methylsulfonyl)" should read -- (4-(4-(Methylsulfonyl)--.

Column 13, line 24, "4-(4-methyl-" should read -- 4-(4-(methyl- --.

Column 14, line 16, "1-(4-Methylthio)" should read -- 1-(4-(Methylthio)--.

Column 14, line 43, "1-(4-methylsulfinyl)" should read -- 1-(4-(methylsulfinyl)--.

UNITED STATES PATENT AND TRADEMARK OFFICE
CERTIFICATE OF CORRECTION

PATENT NO. : 4,349,568

DATED : September 14, 1982

INVENTOR(S) : Lowell D. Markley, et al.

It is certified that error appears in the above—identified patent and that said Letters Patent is hereby corrected as shown below:

Column 19, line 2, "can readily" should read --can be readily --.

Column 23, Claim 13, line 16, "substitutents" should read --substituents--.

Signed and Sealed this

Nineteenth Day of April 1983

[SEAL]

Attest:

GERALD J. MOSSINGHOFF

Attesting Officer    Commissioner of Patents and Trademarks